United States Patent
Bouschbacher et al.

(10) Patent No.: US 9,555,053 B2
(45) Date of Patent: Jan. 31, 2017

(54) USE OF OLIGOSACCHARIDE COMPOUNDS FOR THE PREVENTION AND TREATMENT OF PATHOLOGICAL SCARS

(75) Inventors: Marielle Bouschbacher, Chambolle-Musigny (FR); Christelle Laurensou, Dijon (FR)

(73) Assignees: LABORATOIRES URGO, Chenove (FR); SOCIETE DE DEVELOPPEMENT ET DE RECHERCHE INDUSTRIELLE, Chenove (FR)

( * ) Notice: Subject to any disclaimer, the term of this patent is extended or adjusted under 35 U.S.C. 154(b) by 142 days.

(21) Appl. No.: 14/131,832

(22) PCT Filed: Jul. 12, 2012

(86) PCT No.: PCT/FR2012/051668
§ 371 (c)(1),
(2), (4) Date: Jan. 9, 2014

(87) PCT Pub. No.: WO2013/007960
PCT Pub. Date: Jan. 17, 2013

(65) Prior Publication Data
US 2014/0141058 A1 May 22, 2014

(30) Foreign Application Priority Data
Jul. 13, 2011 (FR) .................... 11 56436

(51) Int. Cl.
| | | |
|---|---|---|
| *A61L 15/00* | (2006.01) | |
| *A61K 31/7016* | (2006.01) | |
| *A61L 15/44* | (2006.01) | |
| *A61K 9/00* | (2006.01) | |
| *A61K 9/70* | (2006.01) | |
| *A61L 15/28* | (2006.01) | |
| *A61K 31/415* | (2006.01) | |
| *A61K 31/513* | (2006.01) | |
| *A61K 8/34* | (2006.01) | |
| *A61K 8/36* | (2006.01) | |
| *A61K 8/37* | (2006.01) | |
| *A61K 8/60* | (2006.01) | |
| *A61Q 19/00* | (2006.01) | |
| *A61K 8/891* | (2006.01) | |

(52) U.S. Cl.
CPC .......... *A61K 31/7016* (2013.01); *A61K 8/342* (2013.01); *A61K 8/361* (2013.01); *A61K 8/37* (2013.01); *A61K 8/375* (2013.01); *A61K 8/60* (2013.01); *A61K 8/891* (2013.01); *A61K 9/0014* (2013.01); *A61K 9/7015* (2013.01); *A61K 31/415* (2013.01); *A61K 31/513* (2013.01); *A61L 15/28* (2013.01); *A61L 15/44* (2013.01); *A61Q 19/00* (2013.01); *A61L 2300/232* (2013.01); *A61L 2300/412* (2013.01)

(58) Field of Classification Search
CPC A61K 31/7016; A61K 9/0014; A61K 9/7015; A61K 8/342; A61K 8/361; A61K 8/37; A61K 8/375; A61K 8/60; A61Q 19/00; A61L 2300/232; A61L 2300/412
See application file for complete search history.

(56) References Cited

U.S. PATENT DOCUMENTS

| | | | | |
|---|---|---|---|---|
| 4,912,093 | A * | 3/1990 | Michaeli | A61K 31/70 514/16.7 |
| 5,618,798 | A * | 4/1997 | Bar-Shalom | A61K 8/02 514/25 |
| 5,908,836 | A * | 6/1999 | Bar-Shalom | A61K 8/26 514/23 |
| 2010/0204174 | A1 * | 8/2010 | Laurensou | A61K 8/8158 514/53 |

FOREIGN PATENT DOCUMENTS

| | | | |
|---|---|---|---|
| EP | 0230023 A2 * | 7/1987 | ............. A61K 31/70 |
| FR | 2824474 | 11/2002 | |
| FR | 2916355 | 11/2008 | |
| FR | 2953522 | 6/2011 | |
| WO | 2002/089818 | 11/2002 | |
| WO | 03/035656 A1 | 5/2003 | |

OTHER PUBLICATIONS

Birol et al., "The effect of sucralfate, an agent for gastroprotection on the healing of split thickness skin graft donor sites," Eur. J. Plastic Surgery, 30(1):25-28 (2007) XP019513152.
International Search Report in PCT/FR2012/051668 dated Oct. 2, 2012.
The Patent Office of the People's Republic of China, Notification of the First Office Action, Application No. 2012800340892, dated Apr. 3, 2015.

* cited by examiner

*Primary Examiner* — Nannette Holloman
(74) *Attorney, Agent, or Firm* — McAndrews, Held & Malloy, Ltd.

(57) ABSTRACT

The present invention relates to a compound selected among the synthetic polysulphated oligosaccharides having 1 to 4 ose units and the salts and complexes thereof to be used for the treatment of wounds resulting in pathological scars selected among hypertrophic, retractile or atrophic scars. Said use is preferred in particular in patients that have a predisposition to developing hypertrophic, retractile or atrophic scars. According to a second aspect, the invention also relates to said compound for the use thereof in order to inhibit the differentiation of fibroblasts into myofibroblasts during the cicatrisation of wounds resulting in pathological scars selected among hypertrophic, retractile or atrophic scars.

11 Claims, 3 Drawing Sheets

Control without TGFbeta | Differentiated control + TGFbeta | Control without TGFbeta | Differentiated control + TGFbeta

+ KSOS

FIGURE 1 (D)

Percentage differentiated cells

+ KSOS

FIGURE 2

USE OF OLIGOSACCHARIDE COMPOUNDS FOR THE PREVENTION AND TREATMENT OF PATHOLOGICAL SCARS

The present application is filed pursuant to 35 U.S.C. 371 as a U.S. National Phase application of International Patent Application No. PCT/FR2012/051668, which was filed Jul. 12, 2012, claiming the benefit of priority to French Patent Application No. 1156436, which was filed on Jul. 13, 2011. The entire text of the aforementioned applications is incorporated herein by reference in its entirety.

The subject of the present invention is a compound chosen from synthetic polysulfated oligosaccharides having 1 to 4 monosaccharide units, the salts thereof, or the complexes thereof, for use thereof in treating wounds resulting in pathological scars.

The healing of a wound is a natural biological phenomenon, human and animal tissues being capable of repairing localized lesions by means of repair and regeneration processes which are specific to them.

The rapidity and the quality of the healing of a wound depend on the general condition of the affected organism, on the etiology of the wound, on the condition and the location of the wound, and on the possible occurrence of an infection, and also on genetic factors possibly predisposing to healing disorders.

The natural healing of a wound takes place mainly according to three successive phases, each of these phases being characterized by specific cell activities which cause the repair process to progress according to precise chronological sequences: the inflammatory phase, the granulation phase (or proliferative phase) and the scar formation phase.

The first phase, the inflammatory phase, begins as soon as blood vessels are ruptured, which triggers the formation of a clot (blood coagulation) mainly composed of fibrin and fibronectin and which will constitute a provisional matrix. This matrix partly fills the lesion and will enable the migration within the damaged area of the inflammatory cells recruited in order to carry out detersion of the wound. The platelets present will also release factors (for example cytokines, growth factors) enabling the recruitment of the healing cells, such as inflammatory cells (neutrophil polymorphonuclear cells and macrophages), fibroblasts and endothelial cells.

The second phase corresponds to the development of the granulation tissue. Colonization of the wound by fibroblast proliferation is first observed. Migration of the endothelial cells from healthy blood vessels will then enable neovascularization, or angiogenesis, of the damaged tissue. In the granulation tissue, the fibroblasts are activated and will differentiate into myofibroblasts with considerable contractile properties, generated by actin microfilaments, enabling contraction of the wound. These microfilaments are expressed by a protein: α-smooth muscle actin. These myofibroblasts therefore play a major role in the formation and maturation of the granulation tissue which will result in healing of the lesion. Keratinocyte migration and reconstruction of the epidermis then take place.

The third phase of the repair process, which is the formation of the scar or maturation, is accompanied by remodeling of the granulation tissue. A part of the extracellular matrix is digested by proteases (essentially matrix metalloproteases (MMPs) and elastases), and a gradual reorganization of the extracellular matrix is observed. Gradually, collagen type III, predominant in the granulation tissue, is replaced with collagen type I, the main matrix component of the dermis. At the end of the maturation phase, the fibroblasts, myofibroblasts and vascular cells experience a reduction in their proliferation and/or their activity. The excess cells then die by apoptosis. In parallel with the remodeling of the extracellular matrix and with the apoptosis of the excess cells, the inflammatory state gradually decreases. This phase is the longest: after about a year, the scar becomes remodeled, it is no longer red, nor rigid, and no longer causes pain and it levels out.

However, in certain cases, the healing is not so successful, and pathological scars may form. The term healing disorders is then used. The latter are conventionally defined as disruptions of healing and group together several phenomena:

chronic ulcers, which are wounds which take a very prolonged time to heal, or which do not heal at all. In certain cases, venous ulcers for example, the wounds can remain atonic for several months without the granulation tissue forming or the healing beginning (*"Managing chronic venous leg ulcers: time for a new approach?"* Brown A. J Wound Care. 2010 February; 19(2):70-4. Review);

atrophic scars, exhibiting a loss of substance, resulting in particular from external traumas or from skin pathologies such as severe acne or chickenpox. These scars exhibit more or less deep retractions of the surface of the skin, thus giving it a pockmarked appearance (M. Chivot, H. Pawin, C. Beylot, O. Chosidow, B. Dreno, M. Faure, F. Poli, J. Revuz—*Cicatrices d'acne: épidémiologie, physiopathologie, clinique, traitement* [Acne scars: epidemiology, physiopathology, clinical aspect, treatment]—Ann. Dermatol. Venereol. 2006; 133:813-24);

hypertrophic scars in which the granulation tissue hyperproliferates abnormally (*"Cellular and molecular pathology of HTS: basis for treatment."* Armour A, Scott P G, Tredget EE. Wound Repair Regen. 2007 September-October; 15 Suppl 1:S6-17. Review. Erratum in: Wound Repair Regen. 2008 July-August; 16(4): 582) and which can in particular occur when the wound reaches the reticular dermis (also called the deep dermis), rich in collagen;

retractile scars are, for their part, caused by a contracting of the area of healing which pulls on the neighboring tissues. They are most commonly the result of burns in certain specific anatomical areas.

Healing disorders therefore group together pathologies which are very different than the normal healing process.

The present invention takes an interest more particularly in wounds which create hypertrophic scars and retractile scars, or even atrophic scars (severe-acne scars).

Methods for treating pathological scars, once said scars are formed, are widely described in the literature. This may, for example, involve "pressotherapy", carried out with elastic compressive clothing, or "corticotherapy" by injection of cortisone-based products into the scar. For atrophic scars, laser or peeling treatments are often used. However, these treatments are sometimes invasive, and most commonly require follow-up for several months, or even years, which is restrictive for the patient.

The document "The effect of sucralfate, an agent for gastroprotection on the healing of split thickness graft donor sites" by Birol Civelek published in *European Journal of Plastic Surgery* (2007), vol. 30, pages 25-28, describes the treatment with sucralfate of wounds resulting from removal of skin for the purpose of a graft. However, the wounds studied in said document cannot result in hypertrophic scars. This is because, as explained, for example, in the document "Greffes cutanées" [Skin grafts] by Revol et al., published in

*Techniques chirurgicales—Chirurgie plastique reconstructrice et esthétique* [Surgical techniques—Reconstructive and esthetic plastic surgery], (2010), 45-070, a thin skin graft must be taken in such a way as to keep epithelial fragments in the donor site and to take keratinocytes from the basal layer in the graft. Thus, the electric dermatome must pass at the level of the dermal crests or papillae, which amounts to creating a wound in the papillary dermis, i.e. the superficial layer of the dermis. Thus, a wound resulting from taking a thin skin graft does not reach the reticular dermis, i.e. the deep dermis, and does not therefore create disorganization of the deep parts of the dermis. Thus, taking thin skin samples cannot result in hypertrophic scars. On the other hand, it is known that hypertrophic scars can occur on a donor site, when a full-thickness skin graft is performed, i.e. when a layer of skin comprising the epidermis, the dermis and its pilosebaceous appendages is taken, which is not the case in said prior art document.

Finally, it should be noted that, in the document Birol Civelek et al., whether or not the wounds are treated with sucralfate, they do not subsequently develop hypertrophic scars, which clearly confirms that these wounds are not able to result in hypertrophic scars, independently of their treatment.

It would therefore be desirable to treat, upstream, preventively, wounds which result in pathological scars so as to limit the abnormal hyperproliferation or abnormal fibrosis of the granulation tissue during the healing, and thus to reduce the risk of pathological scar formation.

A subject of the invention, according to a first aspect, is a compound chosen from synthetic polysulfated oligosaccharides having 1 to 4 monosaccharide units, the salts thereof, or the complexes thereof, for use thereof in treating wounds resulting in pathological scars, preferably chosen from hypertrophic or retractile scars, or even atrophic scars.

A subject of the invention is also, according to a second aspect, a compound chosen from synthetic polysulfated oligosaccharides having 1 to 4 monosaccharide units, the salts thereof, or the complexes thereof, for use thereof in treating wounds in a subject who has a predisposition to developing hypertrophic or retractile scars, or even atrophic scars.

According to another embodiment, the invention consists of a potassium salt of sucrose octasulfate for use thereof in treating wounds resulting in pathological scars chosen from severe-acne scars.

This treatment is in particular suitable for treating pathological scars of all types and of all sizes, whatever their location. Furthermore, in contrast to the usual treatments applied after scar formation, the treatment according to the present invention is used preventively on wounds with a risk of pathological scar formation.

In a normal wound healing process, it is important to promote the wound closing phenomenon in order to avoid, for example, invasion of the wound by microorganisms or foreign substances, and consequently infection of the wound. By way of example, document FR-A-2916355 teaches accelerating fibroblast proliferation and/or differentiation using a particular copolymer for promoting healing speed. It is then desirable to promote keratinocyte migration in order to reconstitute the epidermis.

However, in the particular case of hypertrophic scars, the granulation tissue formed by the fibroblasts hyperproliferates abnormally. When the fibroblasts differentiate into myofibroblasts, this excess fibrous tissue contracts, causing outgrowths of denser tissue in the dermis.

It is not therefore desirable, for specific wounds of this type resulting in hypertrophic or retractile pathological scars, to promote myofibroblast proliferation and differentiation.

On the contrary, it is desirable, for wounds of this type creating pathological scars, to control the myofibroblasts with a view to limiting the development of dermal fibrosis.

Thus, a subject of the invention, according to another aspect, is a compound chosen from synthetic polysulfated oligosaccharides having 1 to 4 monosaccharide units, the salts thereof, or the complexes thereof, for use thereof in inhibiting the differentiation of fibroblasts into myofibroblasts during the healing of wounds resulting in pathological scars chosen from hypertrophic or retractile scars, or even atrophic scars.

Surprisingly, the inventors have discovered that the application of the compound according to the invention to wounds capable of resulting in pathological scars makes it possible to effectively prevent the formation of hypertrophic, retractile or atrophic scars.

This application is particularly preferred in subjects who have a predisposition to pathological scar-type development.

The inventors have in fact shown, in the context of the present application, that inhibiting the differentiation of fibroblasts into myofibroblasts makes it possible to control and/or limit abnormal hyperproliferation of the granulation tissue, and/or to limit wound contraction during the healing of wounds resulting in pathological scars, thus improving the quality of the scars formed.

The present invention has also demonstrated that the use of a particular sulfated oligosaccharide compound influences the differentiation of fibroblasts into myofibroblasts.

DESCRIPTION OF THE FIGURES

In particular, FIG. 1 (A) shows the expression of the α-SMA messenger RNA by quantitative RT-PCR under 4 conditions (nondifferentiated control without TGF-β, differentiated control with TGF-β, nondifferentiated control without TGF-β but with KSOS, and differentiated control with TGF-β and KSOS).

FIG. 1 (B) shows the α-SMA protein expression by the Western blot method.

FIG. 1 (C) shows the α-SMA protein expression visualized by immunofluorescence.

FIG. 1 (D) illustrates the percentages of differentiated cells expressing α-SMA.

PATHOLOGICAL SCARS

The present invention is concerned with wounds which create 3 types of pathological scars: hypertrophic scars, retractile scars and atrophic scars.

Hypertrophic or retractile scars have as common origin an initial hyperplastic phase of high intensity and/or lengthy duration, which phase causes an excess of dense fibrous tissue in the non-reorganized dermis. These pathological scars are large, swollen, red and hard and cause itching. They are characterized by an increased deposition of dermal collagen, which comes from the damaged deep layer of the epidermis, of proteoglycans and of fibronectin and tissue water under the epithelium.

Hypertrophic or retractile scars often form after a burn, but can also develop after a deep injury (surgical incision, for example). They remain confined within the limits of the original wound. Microscopically, they exhibit thin collagen fibers and myofibroblasts expressing α-smooth muscle actin in large amounts. The retractions observed in hypertrophic or retractile scars are caused by the contractile activity of myofibroblasts. Thus, myofibroblasts are responsible for the disorganization of the collagen bundles in the deep layer of the dermis. Indeed, collagen bundles are normally flat, but, under the effect of the contraction of the myofibroblasts, they take on a coiled shape which leads to the formation of collagen nodules under the epithelium.

Hypertrophic scars, when they are located at the level of a joint (bending fold) or of a line of tension, can, like retractile scars, result in incapacitating retractions. They are more abundantly vascularized than normal skin, and the vessels are more dilated. After an active phase, which can last one to two years, hypertrophic scars may gradually regress, but they only rarely disappear completely.

Retractile scars are nonfunctional scars in the sense that they limit the functionality of the area on which they occur. They result in a loss of mobility of the area of healing and of the adjacent areas, which can completely limit movements (for example elbow and mobility of the arm).

Atrophic scars are located under the level of the surrounding skin. They form small hollows and appear when too few new connective tissue fibers are produced during the healing process. Severe-acne scars or chickenpox scars are typical examples of atrophic scars. For the purpose of the present invention, the term "severe-acne scars" is intended to mean acne scars which are the result of lesions which reach the layers of the dermis and not only the epidermis. Severe-acne scars are most commonly the result of forms of acne such as nodular acne, acne fulminans, or acne conglobata which cause inflammatory lesions, such as hardened furunculosis-like nodules having a diameter greater than 5 mm (nodular acne) which can progress to fistulae (acne conglobata). Severe-acne scars can take very varied forms. The first form, termed "crater", corresponds to wide round scars, with a depression simulating a flat-bottomed crater. "Ice pick" acne scars, which are small and often deeper than the "crater" scars, give the impression that the skin has been pricked with a pointed instrument. They are the scars which are the most difficult to treat. These scars are the seat of a fibrosis which makes the scar rigid and hampers the usual treatments.

There are a number of factors which promote the appearance of pathological scars; among the risk factors for pathological scar formation, mention may be made of:
 complexion: populations with a dark complexion (of North African or African origin) are much more prone to hypertrophic scars than Caucasian populations. Subjects with a very pale complexion also have, moreover, a tendency to develop hypertrophic scars;
 age: hypertrophic scars are frequent in children, but are rare in elderly subjects;
 hormones: some times of life, associated with strong bursts of hormones (puberty, pregnancy), are also more favorable to the development of abnormal scars and to acne scars;
 location on the body: some parts of the body are more prone to developing pathological scars, such as, for example, areas where there are folds, joint areas, areas of tension (such as the elbow, the shoulder, the thorax), the sternum, the neck, the ears or the face;
 infectious pathologies which create atrophic scars (chickenpox, severe acne).

For the purpose of the present application, the wounds resulting in pathological scars are defined as wounds which reach the dermis, preferably wounds which reach the reticular dermis (also called deep dermis). Thus, the wounds resulting in pathological scars can be defined as wounds having a depth greater than 0.30 mm, more preferentially greater than 0.35 mm and even more preferentially greater than 0.40 mm.

For the purpose of the present application, the wounds resulting in pathological scars can also be defined as being wounds located on certain parts of the body, for instance areas where there are folds, joint areas, areas of tension (such as the elbow, the shoulder, the thorax), the sternum, the neck, the ears or the face.

For the purpose of the present application, the wounds resulting in pathological scars can also be defined as open wounds occurring in subjects who have a predisposition to developing hypertrophic scars, retractile scars or atrophic scars, such as, for example, subjects who have a dark or very pale complexion, children, pubescent adolescents or pregnant women.

The particular oligosaccharide compound according to the invention is therefore of quite particular interest for the treatment of wounds in subjects who have a predisposition to developing hypertrophic or retractile or atrophic scars, such as subjects who have a dark or very pale complexion, children, pubescent adolescents or pregnant women.

Synthetic Polysulfated Oligosaccharides Having 1 to 4 Monosaccharide Units

The oligosaccharides used in the context of the present invention are synthetic oligomers made up of 1 to 4 monosaccharide units, and preferably of 1 or 2 monosaccharide units, generally linked to one another via an alpha or beta glycosidic bond. In other words, they are mono-, di-, tri- or tetrasaccharides, and preferably monosaccharides or disaccharides.

There is no particular limitation regarding the nature of the monosaccharide units of these polysaccharides. They will preferably be pentoses or hexoses. By way of example of monosaccharides, mention may be made of glucose, galactose or mannose. By way of example of disaccharides, mention may be made of maltose, lactose, sucrose or trehalose. By way of example of a trisaccharide, mention may be made of melezitose. By way of example of a tetrasaccharide, mention may be made of stachyose.

The oligosaccharide is preferably a disaccharide, and more preferably sucrose.

For the purpose of the present application, the term "polysulfated oligosaccharide" is intended to mean an oligosaccharide of which at least two, and preferably all, of the hydroxyl groups of each monosaccharide have been substituted with a sulfate group.

The polysulfated oligosaccharide used in the context of the present application is preferably sucrose octasulfate.

The polysulfated oligosaccharides used in the context of the present invention can be in the form of salts or complexes.

By way of example of salts, mention may be made of the alkali metal salts, such as the sodium, calcium or potassium salts; the silver salts; or else the amino acid salts.

By way of example of complexes, mention may be made of the hydroxyaluminum complexes.

In the context of the present invention, compounds which are particularly preferred are the following:
- the potassium salt of sucrose octasulfate;
- the silver salt of sucrose octasulfate; and
- the hydroxyaluminum complex of sucrose octasulfate, commonly called sucralfate.

In particular, in the context of the present invention, the polysulfated oligosaccharides used are preferably the potassium salts rather than the aluminum salts of sucrose octasulfate.

The polysulfated oligosaccharides used in the context of the present invention can be in the form of a micronized powder or in solubilized form.

An example of a polysulfated oligosaccharide used in the context of the present invention is the potassium salt of sucrose octasulfate (known under the abbreviation KSOS), sold in the product Urgotul® Start by Laboratoires URGO.

Additional Active Substance

Generally, the oligosaccharide compounds according to the invention may be used alone or as a mixture of two or more of them, or else in combination with one (or more) other active substance(s).

Generally, the active agents are chosen from antibacterials, antiseptics, painkillers, anti-inflammatories, active agents promoting healing, depigmenting agents, antipruritics, UV-screening agents, calmatives, moisturizing agents and antioxidants, and mixtures thereof.

Generally, the active agents are chosen from:
- antibacterials, such as polymyxin B, penicillins (amoxicillin), clavulanic acid, tetracyclines, minocycline, chlortetracycline, aminoglycosides, amikacin, gentamicin, neomycin, silver and salts thereof (silver sulfadiazine), probiotics, silver salts;
- antiseptics, such as thiomersal, eosin, chlorhexidine, phenylmercuric borate, aqueous hydrogen peroxide solution, Dakin's solution, triclosan, biguanide, hexamidine, thymol, Lugol's solution, iodinated povidone, merbromin, benzalkonium chloride, benzethonium chloride, ethanol or isopropanol;
- painkillers, such as paracetamol, codeine, dextropropoxyphene, tramadol, morphine and its derivatives, or corticoids and derivatives;
- anti-inflammatories, such as glucocorticoids, nonsteroidal anti-inflammatories, aspirin, ibuprofen, ketoprofen, flurbiprofen, diclofenac, aceclofenac, ketorolac, meloxicam, piroxicam, tenoxicam, naproxen, indomethacin, naproxcinod, nimesulide, celecoxib, etoricoxib, parecoxib, rofecoxib, valdecoxib, phenylbutazone, niflumic acid or mefenamic acid;
- active agents which promote healing, such as retinol, vitamin A, vitamin E, N-acetylhydroxyproline, *Centella asiatica* extracts, papain, silicones, essential oils of thyme, of niaouli, of rosemary and of sage, hyaluronic acid, metformin, allantoin, Hema'tîte® (Gattefosse), vitamin C, Tego® Pep 4-17 (Evonik), Toniskin® (Silab), Collageneer® (Expanscience), Timecode® (Seppic), Gatuline® skin repair (Gattefosse), panthenol, PhytoCellTec® Alp Rose (Mibelle Biochemistry), Erasyal® (Libragen), Serilesine® (Lipotec), Heterosides of Talapetraka (Bayer), Stoechiol (Codif), macarose (Sensient), Dermaveil (Ichimaru Pharcos), phycosaccharide AI (Codif) or metformin;
- depigmenting agents, such as kojic acid (Kojic Acid SL®—Quimasso (Sino Lion)), arbutin (Olevatin®—Quimasso (Sino Lion)), the mixture of sodium palmitoylproline and of European water lily extract (Sepicalm®—Seppic) or undecylenoylphenylalanine (Sepiwhite®—Seppic),
- antipruritics: hydrocortisone, enoxolone, diphenhydramine, locally applied anti H1 antihistamine,
- moisturizing active agents, such as Xpermoist® (Lipotec), hyaluronic acid, urea, fatty acids, glycerol, waxes or Exossine® (Unipex),
- UV-screening agents, such as Parsol® MCX or Parsol® 1789,
- calmatives, such as camomile, bisabolol, Zanthalene®, glycyrrhetenic acid, tanactin (CPN) or Calmiskin® (Silab),
- antioxidants, such as vitamin E.

According to one preferred embodiment, the oligosaccharide compounds according to the invention may be used in combination with an antioxidant.

Galenic Form

The compounds used in the context of the present invention may be employed in a galenic formulation, for instance a gel, a solution, an emulsion, a cream, granules or capsules of variable size ranging from a nanometer or micrometer to a millimeter, which will allow them to be applied directly to the wound. Alternatively, the compounds used in the context of the present invention may be employed in a solution for subcutaneous injection.

If they are employed as a mixture of two or more of them or alternatively in combination with one or more other active substances, these compounds may be incorporated into the same galenic formulation or into distinct galenic formulations.

Of course, the amount of synthetic polysulfated oligosaccharides according to the invention used in the galenic formulation is adjusted according to the desired kinetics and also the specific constraints linked to its nature, solubility, heat resistance, etc.

Generally, when it is used in a galenic formulation, the synthetic polysulfated oligosaccharide compound according to the invention may be incorporated in a content of between 0.1 and 50% by weight relative to the total weight of the formulation.

Dressing

Preferentially, the synthetic polysulfated oligosaccharide compounds used in the context of the present invention, or a galenic formulation containing them, will be integrated into a dressing.

The synthetic polysulfated oligosaccharide compounds, and in particular the potassium salt of sucrose octasulfate or a galenic formulation containing it, may be incorporated into any component of the structure of a dressing with the proviso that this compound can directly or indirectly come into contact with the surface of the wound.

Preferably and in order to promote a rapid action, this compound (or a galenic formulation containing it) will be incorporated into the layer of the dressing which comes into contact with the wound or deposited on the surface of the dressing which comes into contact with the wound.

Advantageously, the potassium salt of sucrose octasulfate (or a galenic formulation containing it) may thus be continuously or discontinuously deposited onto the surface intended to come into contact with the wound:
- either in liquid form, for example by spraying a solution or suspension containing it;
- or in solid form, for example by sieving a powder containing it.

The layer or surface which comes into contact with the wound may consist, for example, of an absorbent material such as a hydrophilic absorbent polyurethane foam; a textile material such as a compress, for example a nonwoven, a film, a web of fibers; an absorbent or nonabsorbent adhesive material; an adherent or non-adherent interface structure.

Generally, it will be possible to adjust the galenic form or the structure of the dressing in order to obtain a rapid or delayed specific release profile for the potassium salt of sucrose octasulfate, as required.

Of course, the amount of potassium salt of sucrose octasulfate used in the galenic formulation or in the dressing will be adjusted according to the desired kinetics and also the specific constraints linked to its nature, solubility, heat resistance, etc.

For the purpose of the present application, the term "dressing" is intended to denote any type of dressing used for the treatment of wounds.

Typically, a dressing comprises at least one adhesive or non-adhesive layer or matrix.

The synthetic polysulfated oligosaccharide compounds according to the invention, or a galenic formulation containing them, can be incorporated into any component of the structure of a dressing, for example into the matrix.

Preferably, and in order to promote a rapid action, this compound (or a galenic formulation containing it) can be incorporated into the layer of the dressing which comes into contact with the wound or deposited onto the surface of the layer of the dressing which comes into contact with the wound.

Such depositing techniques are well known to those skilled in the art and some are, for example, described in patent application WO 2006/007814.

In the context of its use in a component of a dressing, the synthetic polysulfated oligosaccharide(s) according to the invention will be incorporated in an amount such that the amount of polysulfated oligosaccharides that is released into the wound exudates is between 0.001 g/l and 50 g/l, and preferably between 0.01 and 10 g/l.

According to one variant of the invention, the synthetic polysulfated oligosaccharide compound according to the invention can be incorporated into an absorbent dressing based on gelling fibers, for instance the product Aquacel® sold by the company Convatec.

Very often, when these dressings are applied, the care staff keep them in place using a bandage or cover them with a secondary component such as a second absorbent dressing or a support bandage. It is therefore useful for the dressing to remain secured to the wound so that the hands of care staff remain free to position these secondary components. Generally, any type of adhesive commonly employed in dressings may be used for this purpose.

In order not to alter the healthy tissues or the edges of the wound, in particular during the removal of the dressing, an adhesive which has the property of adhering to the skin without adhering to the wound will be preferred.

By way of example of such an adhesive, mention may thus be made of adhesives based on silicone or polyurethane elastomers, such as silicone or polyurethane gels, and hydrocolloid adhesives.

Such hydrocolloid adhesives in particular consist of an elastomeric matrix based on one or more elastomers chosen from poly(styrene-olefin-styrene) block polymers in combination with one or more compounds chosen from plasticizers, such as mineral oils, tackifying resins and, if necessary, antioxidants, into which matrix is incorporated a preferably low amount of hydrocolloids (from 3% to 20% by weight), for instance sodium carboxymethylcellulose or superabsorbent polymers such as the products sold under the name Luquasorb® by the company BASF.

According to one preferred embodiment, the synthetic polysulfated oligosaccharide compounds used in the context of the present invention, or a galenic formulation containing them, will be integrated into a dressing comprising a hydrocolloid adhesive, said polysulfated oligosaccharide being incorporated into said adhesive preferably in an amount of between 1% and 15% by weight, more preferably between 5% and 10% by weight, relative to the weight of the adhesive.

The formulation of such hydrocolloid adhesives is well known to those skilled in the art and is described, for example, in patent applications FR 2 783 412, FR 2 392 076 and FR 2 495 473.

The use of an adhesive net on the nonwoven makes it possible particularly advantageously to decrease or avoid the risk of small fibrils of the textile material coming into contact with the wound and attaching to the tissues, thus causing a painful sensation upon removal, or even an obstacle to the wound healing process. It also makes it possible to better regulate the flow of liquid at the level of the textile material and to reduce or eliminate the risks of gel blocking, resulting from the use of superabsorbent fibers, which in fact limit the absorption capacity of the nonwoven.

According to one preferred embodiment variant of the present invention, the synthetic polysulfated oligosaccharide compound according to the invention is incorporated into such an adhesive at a concentration compatible with its solubility and its heat resistance.

On the basis of these criteria, the synthetic polysulfated oligosaccharide compound according to the invention is preferably used in an amount of between 1% and 15% by weight, and more preferably between 5% and 10% by weight, relative to the total weight of the adhesive.

If it is desired to increase the absorption of this nonwoven dressing, it will be possible to combine the latter with an additional absorbent layer, and preferably an absorbent layer which does not gel, such as, in particular, a compress such as that used in the product Urgotul® Duo or Urgotul® Trio, an absorbent hydrophilic foam, preferably a hydrophilic polyurethane foam which has an absorption capacity greater than that of the nonwoven, such as that used in the product Cellosorb®.

According to one preferred embodiment, the synthetic polysulfated oligosaccharide compound according to the invention is incorporated into a nonwoven dressing, combined with an additional absorbent layer, and preferably an absorbent layer which does not gel, such as in particular a compress.

According to another preferred embodiment, the synthetic polysulfated oligosaccharide compound according to the invention is incorporated into a nonwoven dressing, combined with an additional absorbent layer, and preferably an absorbent layer which does not gel, such as in particular an absorbent hydrophilic foam, preferably a hydrophilic polyurethane foam with an absorption capacity greater than that of the nonwoven.

The nonwoven and the foam can be combined by techniques well known to those skilled in the art, for example by hot calendering, using a hot-melt powder based on TPU/polycaprolactone polymers.

This technique is commonly used for bonding together nonwovens intended for the medical market.

Finally, this foam or the nonwoven (when the latter is used alone) can be covered with a support to protect the wound from the exterior.

This support can be of larger size than the other layers and can be made adhesive continuously or discontinuously on its side which comes into contact with the wound in order to optimize holding of the dressing in place during use, in particular if the wound is located on areas of the body that are not flat.

This support and its adhesive are preferably impermeable to fluids but very permeable to water vapor in order to allow optimal management of the exudates absorbed by the dressing and to avoid problems of maceration.

Such supports are well known to those skilled in the art and consist, for example, of films that can breathe and are impermeable, such as polyurethane films, or foam/film or nonwoven/film complexes.

Additives

In addition to the active agents, the oligosaccharide compounds according to the invention may be used in combination with one (or more) other active substance(s).

The additives commonly used in the preparation of dressings can in particular be chosen from fragrances, preservatives, vitamins, glycerol, citric acid, etc.

The activity of the synthetic polysulfated oligosaccharides according to the invention has been demonstrated in the following nonlimiting examples.

EXAMPLES

Example 1

Demonstration of the Effect of the Potassium Salt of Sucrose Octasulfate (KSOS) on Myofibroblast Differentiation 1. Culture of Normal Human Dermal Fibroblasts (NHDFs)

Cultures of normal human dermal fibroblasts (NHDFs) were prepared in DMEM/F12 culture medium (sold by the company Invitrogen) supplemented with 10% of fetal calf serum (sold by the company Invitrogen), with 5 µg/ml of insulin (sold by the company Promokine) and with 1 ng/ml of bFGF (sold by the company Promokine).

2. Induction of Differentiation

The differentiation of the fibroblasts into myofibroblasts was then induced.

Figure 1:
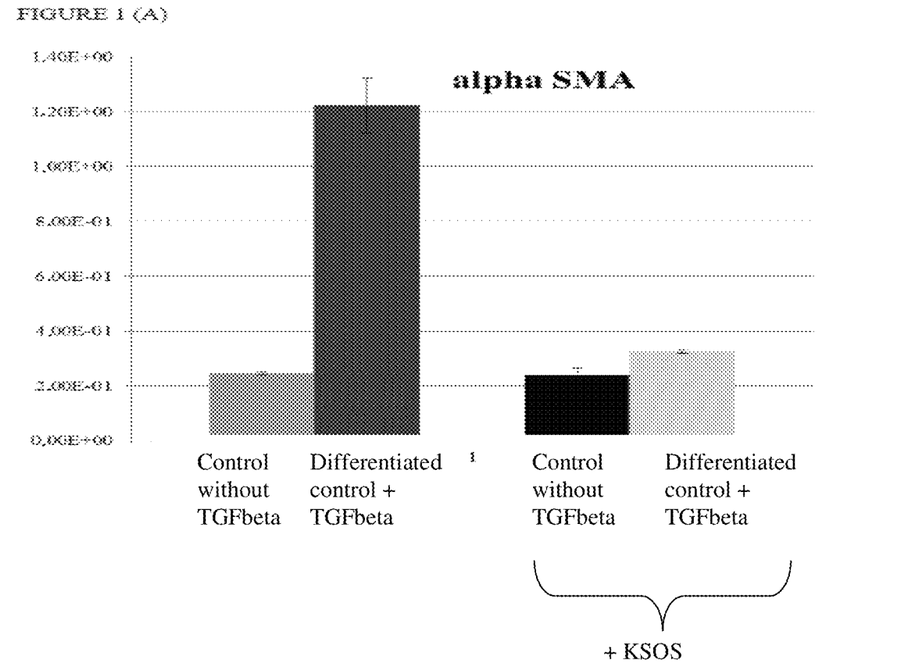
FIG. 1 illustrates the effect of the potassium salt of sucrose octasulfate KSOS on the differentiation of fibroblasts into myofibroblasts.

For this, the NHDF cultures were placed in a P100 dish coated with collagen at 5 µg/ml in DMEM/F12 medium supplemented with 10% of fetal calf serum and supplemented with 10 ng/ml of TGF-β(sold by the company Promocell), which is a growth factor that controls cell proliferation and differentiation (differentiated control in FIG. 1).

A nondifferentiated control was also prepared using cultures in DMEM/F12 supplemented with 10% calf serum without TGF-β.

The KSOS was added to the control and differentiated-control cultures to determine its effect on differentiation, in a proportion of 2 mg/ml.

The results were analyzed after 4 days of culture.

3. Demonstration of the Inhibition of Fibroblast Differentiation

In order to demonstrate the inhibition of the differentiation of the fibroblasts into myofibroblasts, the expression of α-SMA mRNA was measured by quantitative RT-PCR, and the presence of the α-SMA protein was detected by the Western blot method. For the measurement of the inhibitory effect of the compound according to the invention, KSOS was added at 2 mg/ml to the cultures undergoing differentiation.

By quantitative RT-PCR: the mRNA was extracted using the Trizol, chloroform and isopropanol method.

By the Western blot method: total cell extracts were prepared and a Western blot was carried out. The antibodies used are rabbit anti-α-SMA and mouse anti-actin antibodies (sold by Promega).

The differentiation results on D4 clearly demonstrate the induction of α-SMA expression in the cultures in the presence of TGF-β and the inhibition of this induction when KSOS is added (FIG. 1).

Immunofluorescence: cell cultures were prepared in 12-well plates on glass coverslips coated with collagen. The cells were fixed with 4% formaldehyde and permeabilized with Triton. The immunolabeling is carried out using DAPI staining (which gives a blue color) for the cell nuclei, a rabbit anti-α-SMA antibody and an anti-rabbit secondary antibody coupled to Cys3 (sold by Promega).

The number of differentiated cells over the total number of cells is determined by cell counting. The diagram of FIG. 1 (D) gives the percentages of differentiated cells.

Here again, the addition of KSOS causes an inhibition of the differentiation normally generated by TGF-β.

Example 2

Demonstration of the Effect of the Potassium Salt of Sucrose Octasulfate (KSOS) on Collagen Lattice Retraction 1. Preparation of Collagen Lattices The collagen lattices were obtained by seeding $0.8 \times 10^6$ normal human dermal fibroblasts (NHDFs) in a gel of collagen type I with a final concentration of 1.3 mg/ml.

2. Demonstration of the Effect of the Potassium Salt of Sucrose Octasulfate on Collagen Lattice Retraction A dressing (sold under the trade name Urgotul Start) comprising 7.5% of the potassium salt of sucrose octasulfate was applied to the surface of the collagen lattices.

A control series, without dressing, was carried out in order to evaluate the normal contraction of the collagen gel by the seeded NHDFs.

Likewise, a positive control was carried out by adding TGF-β at a concentration of 10 ng/ml in order to visualize the strong contraction induced by the NHDFs highly differentiated into myofibroblasts.

The incubation was maintained up to 7 days.

3. Results

Figure 2:
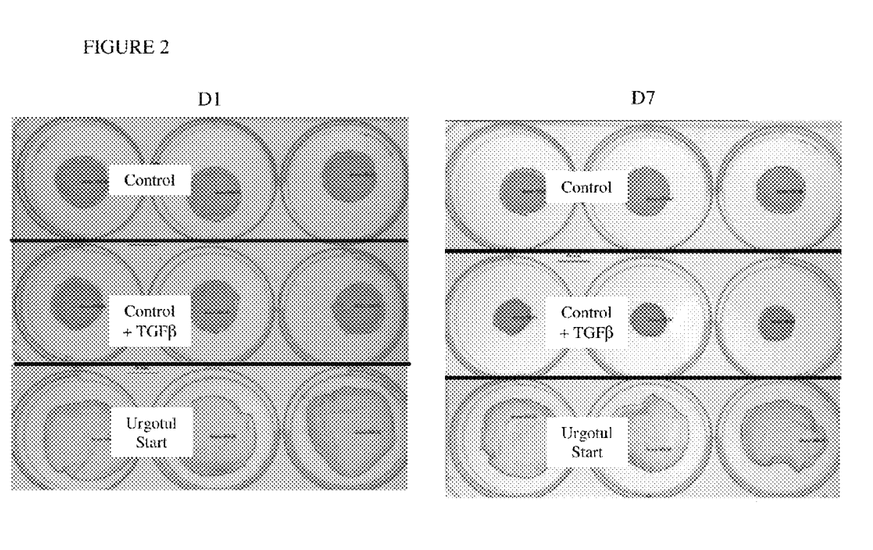
FIG. 2 illustrates, by means of photographs of the collagen lattices on D1 and D7 under the various conditions, the collagen lattice contraction-inhibiting effect of the Urgotul® Start dressing containing the potassium salt of sucrose octasulfate (KSOS) after 1 and 7 days of culture.

The effects of the potassium salt of sucrose octasulfate on the retraction of the collagen lattices was observed by means of photographic analysis (FIG. 2) and image analysis measurement of the area of the lattices once contracted.

The results of the measurements of the average area of the collagen lattices are given in the following table:

| | Treatment | Average of the areas (mm$^2$) | % relative to the control |
|---|---|---|---|
| Day 1 | Control | 229.7 | 100 |
| | Control + TGF-β | 217.3 | 95 |
| | Urgotul Start comprising KSOS according to the invention | 533.8 | 232 |

-continued

| Treatment | | Average of the areas (mm$^2$) | % relative to the control |
|---|---|---|---|
| Day 4 | Control | 191.0 | 100 |
| | Control + TGF-β | 145.9 | 76 |
| | Urgotul Start comprising KSOS according to the invention | 481.4 | 252 |
| Day 7 | Control | 174.7 | 100 |
| | Control + TGF-β | 97 | 56 |
| | Urgotul Start comprising KSOS according to the invention | 484.6 | 277 |

Under the control conditions, the lattices gradually contracted between day 1 and day 7. The application of the Urgotul Start dressing comprising the potassium salt of sucrose octasulfate clearly slowed the contraction of the lattices.

This result demonstrates that the treatment with KSOS limits the contraction of the collagen lattices, which is very positive for the treatment and prevention of pathological scars with significant levels of scar retraction.

Example 3

A formulation of solvent-based filmogel type comprising a synthetic polysulfated oligosaccharide according to the invention, having the following composition, was prepared:

| Constituents | % |
|---|---|
| Nitrocellulose | 12.800 |
| Castor oil | 11.000 |
| Absolute ethanol | 24.90 |
| Ethyl acetate | 49.70 |
| UV-screening agents | 1.500 |
| Potassium salt of sucrose octasulfate KSOS | 0.100 |

The nitrocellulose was diluted in an ethyl acetate/absolute ethanol mixture. The castor oil, the UV-screening agents and the KSOS were then added until dissolution so as to obtain a composition of filmogel type.

Example 4

A formulation of water-based filmogel type comprising a synthetic polysulfated oligosaccharide according to the invention, having the following composition, was prepared:

| Constituents | % |
|---|---|
| Demineralized water | 93.200 |
| Thickener | 0.500 |
| Sorbitol | 2.000 |
| Dextran | 1.000 |
| Potassium salt of sucrose octasulfate KSOS | 1.000 |
| Methylparaben | 0.050 |
| Propylparaben | 0.050 |
| Phenoxyethanol | 0.700 |
| 10% NaOH | 1.500 |

The thickener was dispersed in the water with vigorous stirring, and then the sorbitol and the dextran were added while heating to 40° C. so as to obtain better solubility.

The KSOS, the parabens and the phenoxyethanol were added and the mixture was left to stir in order to homogenize. It was then left to cool to ambient temperature by stopping the heating, while if required adjusting the water loss. Finally, the mixture was neutralized with sodium hydroxide and left to stir for 10 minutes before stopping the stirring.

Example 5

A formulation in the form of a cream comprising a synthetic polysulfated oligosaccharide according to the invention, having the following composition, was prepared:

| Constituents | % |
|---|---|
| Oil-in-water surfactant | 5.000 |
| Emulsifying wax | 2.000 |
| Stearic acid | 1.000 |
| Isodecyl isononanoate | 6.000 |
| Silicone oil (Decamethylcyclopentasiloxane) | 4.000 |
| Emollient ester (myristyl lactate) | 5.000 |
| Demineralized water | 62.100 |
| Thickener | 0.300 |
| Glycerol | 5.000 |
| Propylene glycol | 5.000 |
| Potassium salt of sucrose octasulfate KSOS | 0.500 |
| Preservative | 1.500 |
| 10% NaOH | 0.600 |
| Silicone surfactant | 2.000 |

The thickener was dispersed in the water. The glycerol, the propylene glycol, the KSOS and the preservative were added and the mixture was homogenized. It was heated to 70-75° C. When the mixture reached 70-75° C., the amount of water was adjusted and then the mixture was neutralized with 10% sodium hydroxide and the temperature was brought back to 70-75° C.

At the same time, the oil-in-water surfactant, the emulsifying wax, the stearic acid, the isodecyl isononanoate, the silicone oil (decamethylcyclopentasiloxane) and the emollient ester (myristyl lactate) were mixed together and heated to 70-75° C.

When the 2 mixtures reached 70-75° C., the second was added to the first with vigorous stirring and the resulting mixture was left to stir hot for 10 minutes.

The silicone surfactant was then added and the resulting mixture was again left to stir hot for 5 minutes.

Finally, the heating was stopped and the mixture was left to cool to ambient temperature, while maintaining sufficient stirring depending on the viscosity of the mixture. The mixture takes on a nonhomogeneous appearance around 35° C., but the cream then becomes smooth and shiny.

The invention claimed is:

1. A method for treating wounds resulting in pathological scars by inhibiting the differentiation of fibroblasts into myofibroblasts, said method comprising applying to said wounds a compound chosen from synthetic polysulfated oligosaccharides having 1 to 4 monosaccharide units, the salts thereof, or the complexes thereof, wherein the pathological scars are chosen from hypertrophic or retractile scars.

2. The method as claimed in claim 1, wherein the compound is chosen from synthetic polysulfated oligosaccharides having 1 or 2 monosaccharide units, and also the salts and complexes of these compounds.

3. The method as claimed in claim 1, wherein the compound is chosen from:
   the potassium salt of sucrose octasulfate;
   the silver salt of sucrose octasulfate; and
   the hydroxyaluminum complex of sucrose octasulfate.

4. The method as claimed in claim 1, wherein the compound is combined with one or more other active substances chosen from antibacterials, antiseptics, painkillers, anti-inflammatories, active agents which promote healing, depigmenting agents, antipruritics, UV-screening agents, calmatives, moisturizing agents and antioxidants, and mixtures thereof.

5. The method as claimed in claim 4, characterized in that the other active substance is chosen from antioxidants.

6. The method as claimed in claim 1, wherein the compound is present in a galenic formulation selected from the group consisting of a gel, a solution, an emulsion, a cream, granules or capsules allowing application directly to the wound.

7. The method as claimed in claim 1, wherein the compound, or a galenic formulation containing it, is integrated into a component of a dressing.

8. The method as claimed in claim 7, wherein said dressing is a nonwoven dressing, combined with an additional absorbent layer.

9. The method as claimed in claim 7, wherein said dressing is a dressing comprising a nonwoven, combined with an additional absorbent layer.

10. The method as claimed in claim 7, wherein the dressing comprises a hydrocolloid adhesive and in that said polysulfated oligosaccharide is incorporated into said adhesive.

11. The method as claimed in claim 1 for treating wounds in a subject who has a predisposition to developing hypertrophic or retractile scars.

* * * * *